United States Patent
Yang et al.

(10) Patent No.: US 10,677,799 B2
(45) Date of Patent: Jun. 9, 2020

(54) CATHEPSIN K AS A MARKER FOR CARTILAGE PRODUCTION, REPAIR AND REGENERATION

(71) Applicant: Rhode Island Hospital, Providence, RI (US)

(72) Inventors: Wentian Yang, Pawtucket, RI (US); Nikhil Thakur, Atlanta, GA (US)

(73) Assignee: Rhode Island Hospital, Providence, RI (US)

( * ) Notice: Subject to any disclaimer, the term of this patent is extended or adjusted under 35 U.S.C. 154(b) by 715 days.

(21) Appl. No.: 13/833,403

(22) Filed: Mar. 15, 2013

(65) Prior Publication Data

US 2014/0044681 A1    Feb. 13, 2014

Related U.S. Application Data

(60) Provisional application No. 61/614,442, filed on Mar. 22, 2012.

(51) Int. Cl.
*A61K 35/32* (2015.01)
*A61K 35/28* (2015.01)
*C12N 5/0775* (2010.01)
*G01N 33/573* (2006.01)
*C12N 5/077* (2010.01)
*G01N 33/50* (2006.01)

(52) U.S. Cl.
CPC .......... *G01N 33/573* (2013.01); *A61K 35/28* (2013.01); *A61K 35/32* (2013.01); *C12N 5/0655* (2013.01); *C12N 5/0662* (2013.01); *G01N 33/5005* (2013.01); *G01N 33/5073* (2013.01); *G01N 2333/96466* (2013.01)

(58) Field of Classification Search
None
See application file for complete search history.

(56) References Cited

U.S. PATENT DOCUMENTS

2005/0152882 A1*  7/2005  Kizer ................. A61F 2/30756
                                                  424/93.7
2009/0155200 A1*  6/2009  Jay ..................... A61K 31/737
                                                  424/78.3

FOREIGN PATENT DOCUMENTS

CA         2669470      *  4/2009

OTHER PUBLICATIONS

Articular Cartilage Restoration—OrthoInfo American Academy of Orthopaedic Surgeons http://orthoinfo.aaos.org/topic.cfm?topic=a00422, Feb. 2009.*
Articular Cartilage Restoration—OrthoInfo America Academy of Orthopaedic Surgeons http://orthoinfo.aaos.org/topic.cfm?topic=a00422, Feb. 2009.*
Cucchiarini et al. "Improved Tissue Repair in Articular Cartilage Defects in Vivo by rAAV-Mediated Overexpression of Human Fibroblast Growth Factor 2." Molecular Therapy vol. 12, No. 2, Aug. 2005.*
Harada et al. "Control of osteoblast function and regulation of bone mass." Nature, vol. 423, May 15, 2003.*

(Continued)

*Primary Examiner* — Blaine Lankford
*Assistant Examiner* — Lauren K Van Buren
(74) *Attorney, Agent, or Firm* — Mintz Levin Cohn Ferris Glovsky and Popeo, P.C.; Ingrid A. Beattie

(57) ABSTRACT

Ctsk is used as a marker to identify, track, and manipulate Ctsk positive cartilaginous stem cells for cartilage repair and regeneration in vitro and in vivo.

16 Claims, 5 Drawing Sheets

Specification includes a Sequence Listing.

(56) References Cited

OTHER PUBLICATIONS

Articular Cartilage Restoration—OrthoInfo America Academy of Orthopaedic Surgeons http://orthoinfo.aaos.org/topic.cfm?topic=a00422, Feb. 2009. (Year: 2009).*
Cucchiarini et al. "Improved Tissue Repair in Articular Cartilage Defects in Vivo by rAAV-Mediated Overexpression of Human Fibroblast Growth Factor 2." Molecular Therapy vol. 12, No. 2, Aug. 2005. (Year: 2005).*
Karlsson et al. "Identification of a stem cell niche in the zone of Ranvier within the knee joint" J. Anat. (2009), 215, pp. 355-363. (Year: 2009).*
Bowen et al. (2011) "Loss-of-Function Mutations in PTPN11 Cause Metachondromatosis, but Not Oilier Disease or Maffucci Syndrome," PLoS Genetics. 7(4):e1002050(1-11).
Sobreira et al. (2010) "Whole-Genome Sequencing of a Single Proband Together with Linkage Analysis Identifies a Mendelian Disease Gene," PLoS Genetics. 6(6):e1000991(1-6).
Yang et al. (2013) "Ptpn11 Deletion in a Novel Cartilage Cell Causes Metachondromatosis by Activating Hedgehog Signalling," Nature. 499(7459):491-495.
Hirada et al. (2003) "Control of osteoblast function and regulation of bone mass," Nature. 423:349-355.

\* cited by examiner

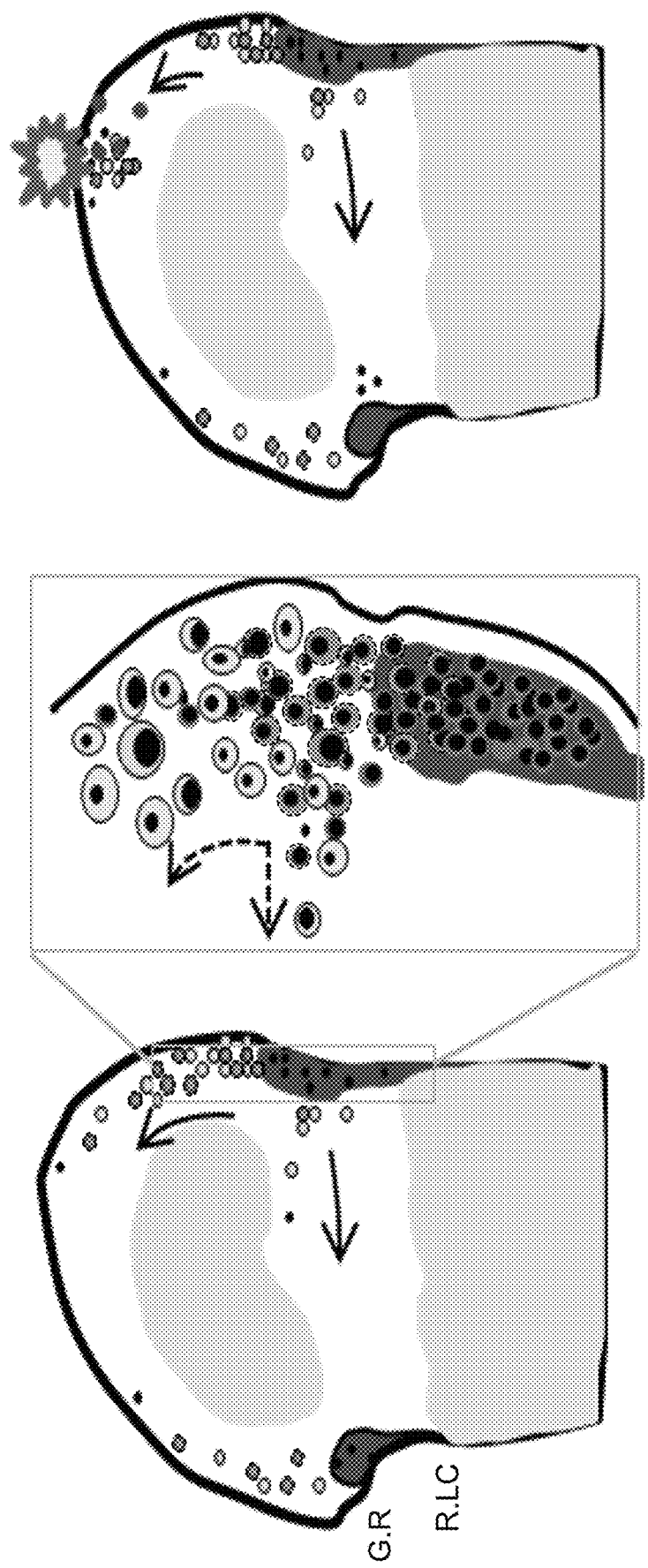

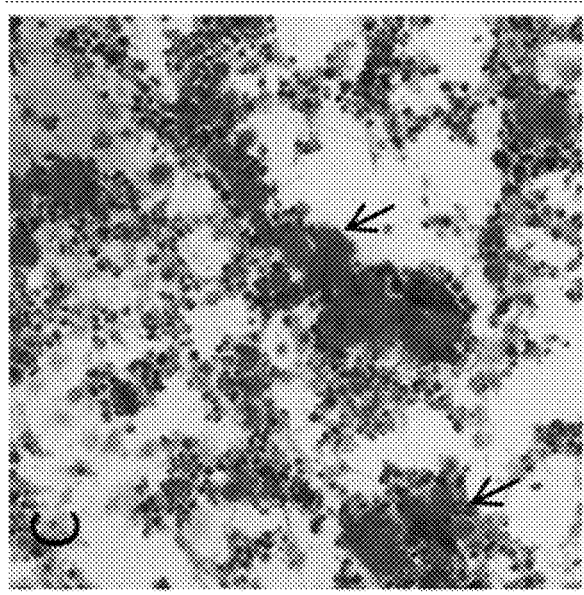
FIG. 2A Alican Blue
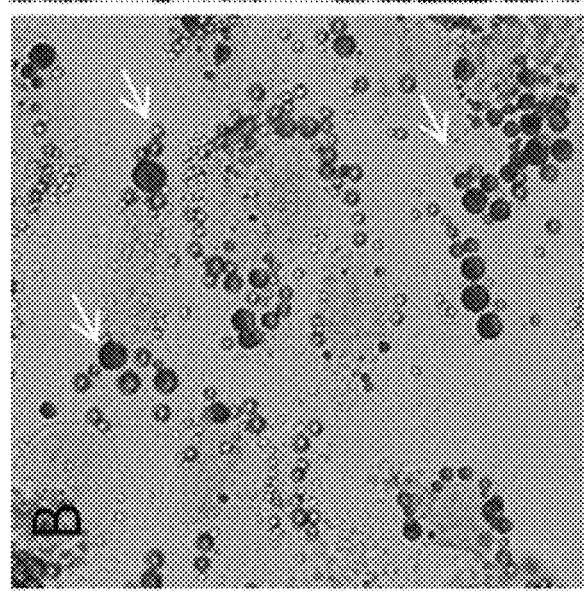
FIG. 2B Oil Red
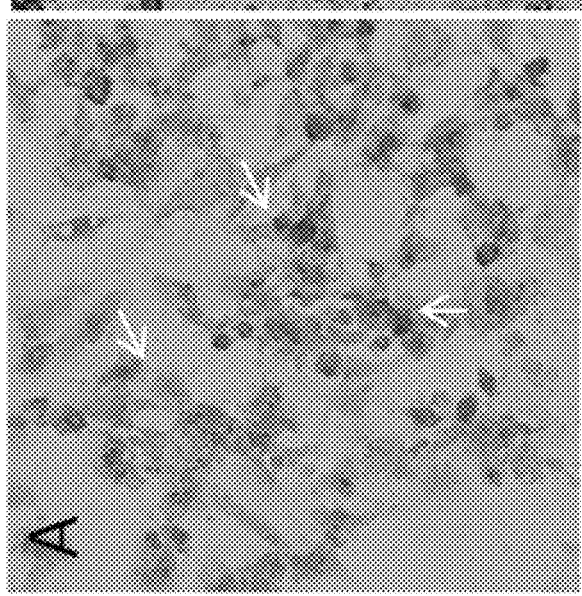
FIG. 2C Alizarin Red

CATHEPSIN K AS A MARKER FOR CARTILAGE PRODUCTION, REPAIR AND REGENERATION

RELATED APPLICATION INFORMATION

This application claims priority to U.S. provisional application Ser. No. 61/614,442, filed on Mar. 22, 2012, the contents of which are hereby incorporated by reference.

GOVERNMENT SUPPORT

This invention was made with Government support under NIH/NCRR P20 RR025179 awarded by the National Institutes of Health. The Government has certain rights in the invention.

INCORPORATION-BY-REFERENCE OF SEQUENCE LISTING

The contents of the text file named "21486-611001US_ST25.txt", which was created on Oct. 24, 2013 and is 8.32 KB in size, are hereby incorporated by reference in their entireties.

FIELD OF THE INVENTION

The invention relates to orthopedics

BACKGROUND OF THE INVENTION

Cathepsin K (Ctsk) is a proteinase that is predominantly expressed in mature osteoclasts and has been used previously to modulate osteoclastic bone resorptive activity and treat bone degenerative disease osteoporosis.

SUMMARY OF THE INVENTION

Ctsk is used as a marker to identify, track, and manipulate Ctsk positive cartilaginous stem cells for cartilage repair and regeneration in vitro and in vivo. For example, cells are isolated from a donor by virtue of the Ctsk expression, purified, and optionally cultured prior to administration (e.g., transplantation) into a recipient joint. The donor and recipient tissues are syngeneic or allogeneic. For example, the donor and recipient tissue are of the same subject, e.g., a human patient.

A method of repairing, restoring, regenerating, or producing articular cartilage comprises introducing into an articulating joint a population of stem cells isolated from an articular cartilage or a perichondrial groove of Ranvier is also within the invention. The methods are suitable for not only humans, but companion animals such as dogs and cats as well as livestock or performance animals such as horses.

A method of identifying a cartilage stem cell or progenitor cell is carried out by contacting a cartilage-derived or joint space-derived population of cells with a cathepsin K-specific reagent such as a Ctsk-specific antibody and detecting binding of reagent to the cells. Detection of specific binding, e.g., by virtue of a detectable marker such as a fluorescent compound such as fluorescein or rhodamine (e.g., FITC, TRITC), cyanine, Alexa fluors, indicates that a cell is a cartilage stem cell or progenitor cell. A method of isolating a cartilage stem cell or progenitor cell is also based on the expression of Ctsk on such cells. The method includes the steps of contacting a cartilage-derived or joint space-derived population of cells with a cathepsin K-specific reagent to yield a mixture of reagent-bound cells (Ctsk-positive cells) and reagent-unbound cells (Ctsk-negative cells), and separating the reagent-bound cells from the reagent-unbound cells to yield a population of reagent-bound cells which comprises isolated cartilage stem cells or progenitor cells, i.e., a population of purified cathepsin K-positive cartilage stem cells. The reagent can then optionally be removed prior to administering cells for therapy. The cells are suspended in a pharmaceutically-acceptable excipient for clinical use.

Compounds described herein, e.g., those used for therapy are purified and/or isolated. As used herein, an "isolated" or "purified" compound, e.g., nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, or 100%, by weight the compound of interest. Purity is measured by any appropriate standard method, for example, by column chromatography, polyacrylamide gel electrophoresis, or HPLC analysis.

Publications, U.S. patents and applications, Genbank/NCBI accession numbers, and all other references cited herein, are hereby incorporated by reference.

BRIEF DESCRIPTION OF THE DRAWINGS

In FIG. 1A, X-gal staining shows that ctsk-expressing cells (black area indicated by the arrow) exist in the groove of Ranvier of one-week-old mice. FIGS. 1B-C are fluorescence images of the frozen sections of knee joint from Ctsk-Cre; Rosa26YFP reporter mice demonstrating that Ctsk positive cells (white) exist in the groove of Ranvier (B ii, iii, arrows) and can migrate towards articular cartilage (C iv,v) and growth plate (arrows). The diagrams in FIG. 1D illustrate the locations of perichondrial groove of Ranvier (G.R) and the Ring of La Croix (R.L.C) (in black) in knee joints. Stem-like cells, their progenitors, and differentiated progeny are denoted by solid black dots, dots surrounded by dotted line, and white dots, respectively in the enlarged area.

FIGS. 2A-C are photomicrographs showing cells differentiated from stem cells purified using Ctsk as a marker. Ctsk positive cartilage cells possess tissue stem cell property Ctsk+perichondrial cartilage cells were purified by FACS from the epiphyseal cartilage prepared from Rosa26YFP; Ctsk-Cre reporter mice. The purified cell population was then subjected to tri-lineage differentiation towards bone (osteoblasts), cartilage (chondrocytes), and fat (adipocytes) tissues. The differentiated cells were then stained with alcian blue, oil red, and alizarin red to evaluate their ability of chondrogenesis, adipogenesis, and bone cell formation, respectively. Images of A, B, and C demonstrated that Ctsk+ cartilage cells are able to form cartilage (A, arrows), fat (B, arrows) and bone cells (C, arrows), respectively, upon proper induction in vitro. Adipogenic differentiation medium: DMEM (low glucose) with FBS (10%), Dexamethasone (1 uM), IBMX (0.5 mM), and Insulin (10 ug/ml); Osteogenic medium: Basic DMEM medium supplemented with 10 mM-glycerol phosphate, 50 uM ascorbic acid, and mBMP (10 ug/ml); chondrogenic medium made by adding 10 ng/ml TGF-β1, 100 ng/ml IGF, and 10 nM dexamethasone, and 100 μM L-ascorbic acid 2-phosphate to basic DMEM.

DETAILED DESCRIPTION

Prior to the invention, there was no correlation between Ctsk and stem cell identification in groove of Ranvier and articular cartilage. Ctsk has now been shown to be useful to identify and modulate cartilaginous stem cells/progenitor cells. Under physiological conditions, the cells derived from perichondrial groove of Ranvier are required for articular cartilage development and homeostasis. In situations in which cartilage damage occurs (such as osteoarthritis and trauma), these cells respond to pathogenic insults and start to expand and repair cartilage damage.

The existence of chondrogenic stem cells and their niches in adult human articular joints has been controversial. The development and homeostasis of epiphyseal cartilage are supported by stem-cell like cells in cartilage. Both the superficial zone of articular cartilage and the perichondrial groove of Ranvier in mammalian joints function as sources for cartilaginous stem cell supply. When articular joint cartilage is damaged, these stem cells can transiently proliferate, differentiate, and form new cartilage to repair the injury.

Figure 1A:
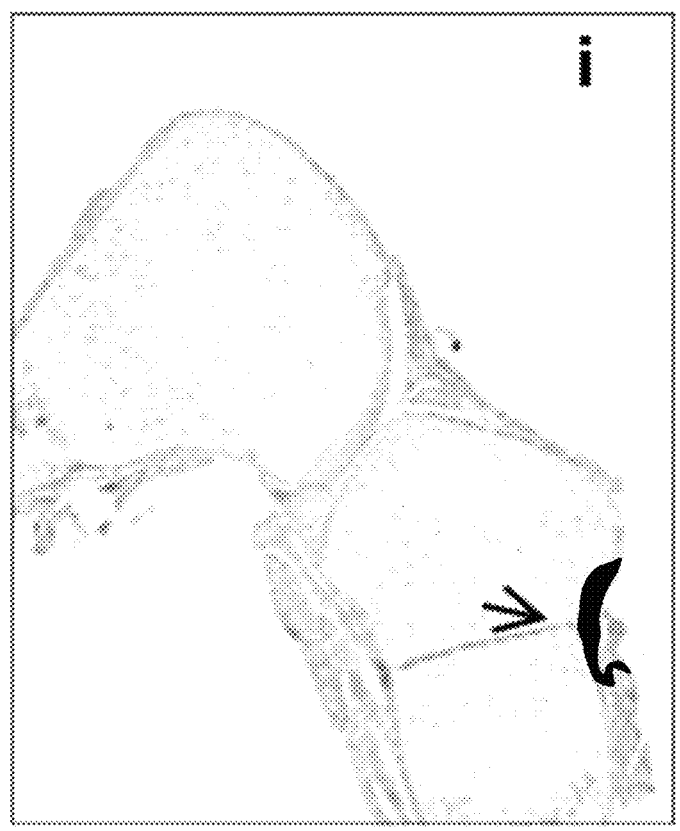
FIGS. 1A-C are photomicrographs and FIG. 1 D is a diagram showing the results of a Ctsk-Cre;Rosa261acZ and Ctsk-Cre;Rosa26YFP reporter study on transgenic mice demonstrating that Ctsk positive cartilaginous cells exist in the perichondrial groove of Ranvier and articular cartilage.
Figure 1B:
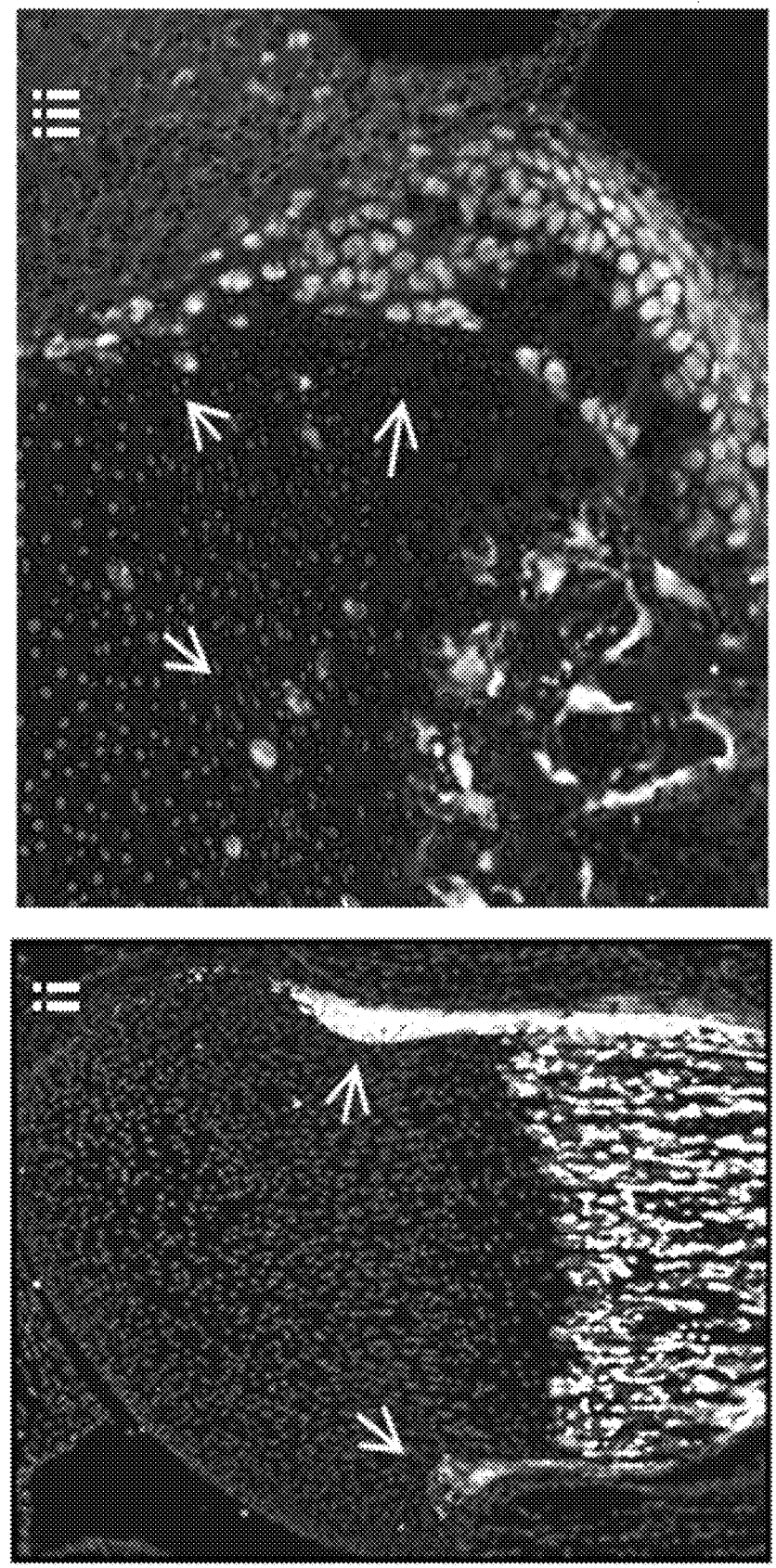
Figure 1C:
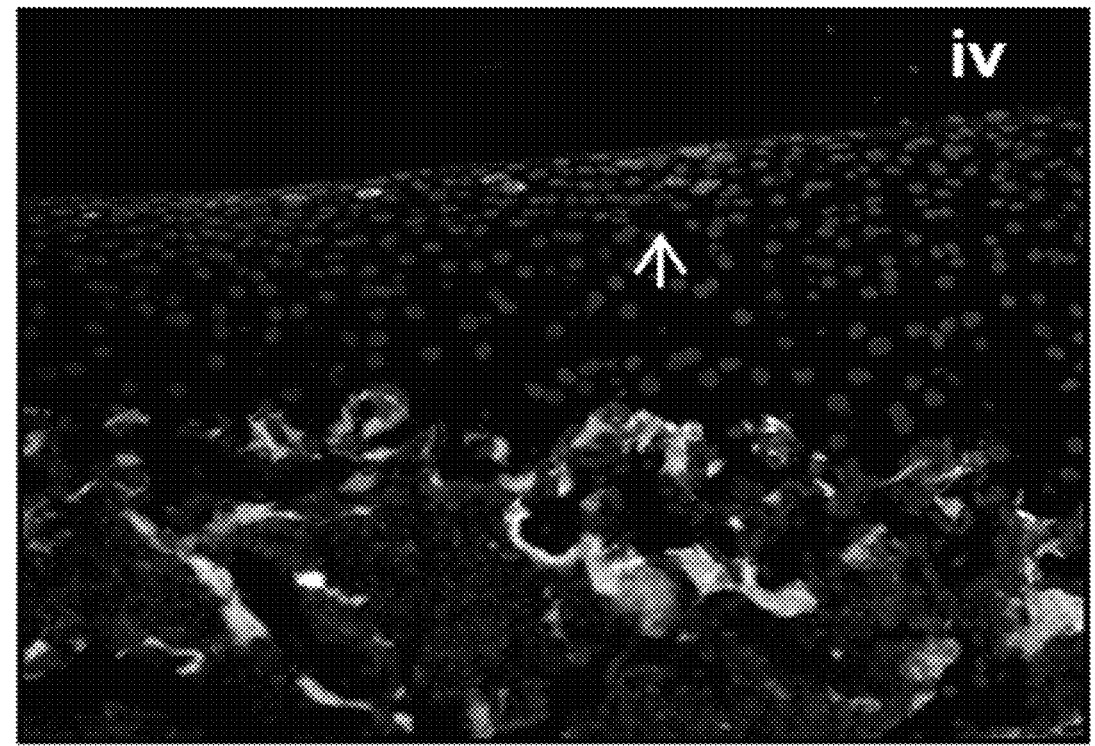
Figure 1C:
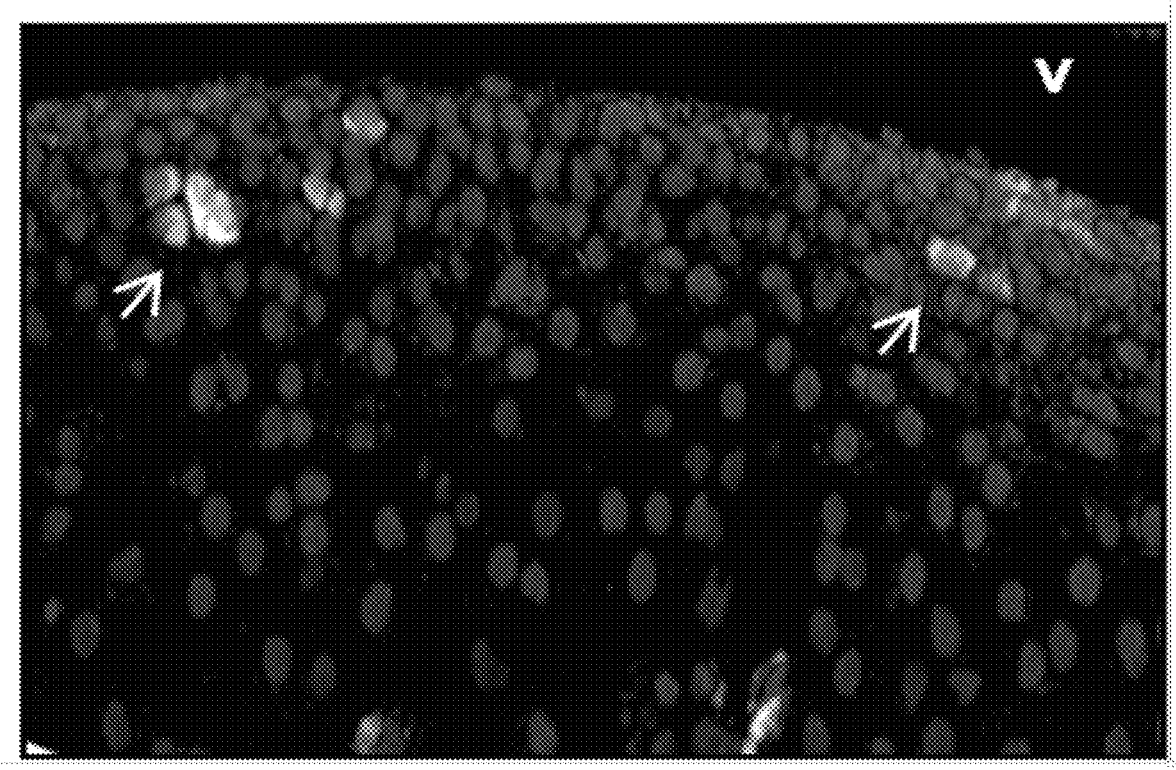

Several surface markers for these stem cells have been identified (such as CD44, CD90, CD105, and Stro1, etc), but prior to the invention there was no effective way to identify and track these cells in vitro and in vivo. By taking tissue/cell-specific Rosa26lacZ and Rosa26EYFP reporter studies, the proteinase cathepsin K (Ctsk) was found to function as a marker that can specifically identify these unique stem cells residing in articular cartilage and perichondrial groove of Ranvier. The data described herein show that these cells, under proper induction in vivo, can proliferate, differentiate, and result in new cartilage formation in a transgenic mice model. (see FIGS. 1A-D and 2A-C). This discovery allows Ctsk as a marker to be used to identify, track, and manipulate Ctsk positive cartilaginous stem cells for cartilage repair and regeneration in vitro and in vivo. By using Ctsk as a specific marker for cartilaginous stem cells/progenitors, these particular stem cell populations are mobilized in vitro and in vivo (or ex vivo) for cartilage repair and regeneration.

The human Cathepsin K sequence is provided below.

orthopedic biologic technology has always been to repair, regenerate damaged cartilage, and reduce the incidence of osteoarthritis. Pharmacologically targeting Ctsk-expressing cartilage stem cell/progenitor population forms the basis of therapeutics using those cells to treat cartilage injury and cartilage degenerative diseases, such as osteoarthritis.

Identification and Purification of Ctsk-Positive Cartilage Cells

Isolation of murine cathepsin K+ epiphyseal cartilage cells was carried out as follows. Epiphyseal cartilage was harvested by dissecting 4 to 6-week-old mice carrying Ctsk-Cre and Rosa26YFP reporter. After washing with PBS briefly, these cartilage tissues were incubated with trypsin-EDTA (0.25%) for 60 minutes at 37° C. to remove any soft tissues. After washing with PBS again, they were further incubated with hyaluronidase (2 mg/ml) for 2 hours and hyaluronidase/collagenase D mixture (1 mg/ml) for 4 hours in DMEM at 37° C. Undigested bony tissues were discarded by filtration, cartilaginous cells released into the solution were collected by centrifugation and cultured in DMEM/F12 medium (1:1) supplemented with 10% of FBS, and 1% of ampicillin and streptomycin or subjected to biological analyses.

Ctsk-expressing cells are identified and purified using Ctsk-specific reagents such as antibodies. Antibodies specific for human and mouse Ctsk are commercially available, e.g., cathepsin K Antibody (E-7): sc-48353 (Santa Cruz Biotechnology, Inc. Dallas, Tex.), Anti-Cathepsin K antibody (ab19027) (Abcam, Cambridge, Mass.), Anti-Cathepsin K Antibody, clone 182-12G5 | MAB3324 (EMD Millipore, Billerica, Mass.), C8243 Sigma Monoclonal Anti-Cathepsin K antibody (Sigma Aldrich, St. Louis, Mo.), M189 Anti-Human Cathepsin K (Clontech, Mountain View, Calif.). Ctsk-expressing cells are then enriched or purified using any of a number of known techniques such as panning, fluorescent activated cell sorting (FACS), and magnetic bead separation in vitro.

Any source of live cartilage tissue serves as a source of Ctsk-expressing cells, e.g., the cells are autologous (cells obtained from the individual to be treated), allogeneic (cells from a HLA-matched related or unrelated donor), or syngeneic (cells from an identical twin or triplet). Ctsk-positive cells are found on the surface of articular cartilage. The cells are harvest using know methods, e.g., arthroscopically or

```
                                                        (SEQ ID NO: 1)
MWGLKVLLLP VVSFALYPEE ILDTHWELWK KTHRKQYNNK VDEISRRLIW EKNLKYISIH 70         80         90        100        110        120
NLEASLGVHT YELAMNHLGD MTSEEVVQKM TGLKVPLSHS RSNDTLYIPE WEGRAPDSVD 130        140        150        160        170        180
YRKKGYVTPV KNQGQCGSCW AFSSVGALEG QLKKKTGKLL NLSPQNLVDC VSENDGCGGG 190        200        210        220        230        240
YMTNAFQYVQ KNRGIDSEDA YPYVGQEESC MYNPTGKAAK CRGYREIPEG NEKALKRAVA 250        260        270        280        290        300
RVGPVSVAID ASLTSFQFYS KGVYYDESCN SDNLNHAVLA VGYGIQKGNK HWIIKNSWGE 310        320
NWGNKGYILM ARNKNNACGI ANLASFPKM

[P43235 (CATK_HUMAN) Reviewed, UniProtKB/Swiss-Prot; Last modified
Mar. 21, 2012. Version 131 or GENBANK AAH16058.1 GI: 16359188; each
of which is hereby incorporated by reference.]
```

Humans, as they are aging, reduce the ability to develop new articular cartilage once cartilage is injured. The holy grail of during a surgical procedure, from a live individual. Alternatively, the cells are harvested from a cadaver donor. A purified population of cells or enriched population contains at least 60%, 70%, 80%, 90%, 95%, 98%, 99% Ctsk-positive cells. For example, a population of cells for therapeutic use, e.g., cell therapy, comprises about 70-80% Ctsk-positive stem cells. Optionally, the cell population is enriched by culturing the cells in vitro.

Therapeutic Applications

The cells purified or enriched as described above are used to treat cartilage disorders such as degenerative joint diseases, e.g., osteoarthritis, or injuries to an articulating joint due to trauma, overuse, or genetic predisposition. The cells are administered to an articulating joint in need of treatment, e.g., a knee, hip, elbow, shoulder, or even vertebra, to repair and restore cartilage.

To treat such joints in vivo, agents that mobilize and/or preferentially stimulate Ctsk-positive cells are administered to the affected joint to mobilize and stimulate the cells to repair and/or restore surface cartilage of the joint. For example, a composition containing IGF (GenBank: AAI48267)

```
                                                           (SEQ ID NO: 2)
  1 MGKISSLPTQ LFKCCFCDFL KVKMHTMSSS HLFYLALCLL TFTSSATAGP ETLCGAELVD

61 ALQFVCGDRG FYFNKPTGYG SSSRRAPQTG IVDECCFRSC DLRRLEMYCA PLKPAKSARS

121 VRAQRHTDMP KTQKYQPPST NKNTKSQRRK GWPKTHPGGE QKEGTEASLQIRGKKKEQRR

181 EIGSRNAECR GKKGK
```
and/or FGF2 (NP_001997)

```
                                                           (SEQ ID NO: 3)
  1 MVGVGGGDVE DVTPRPGGCQ ISGRGARGCN GIPGAAAWEA ALPRRRPRRH PSVNPRSRAA

61 GSPRTRGRRT EERPSGSRLG DRGRGRALPG GRLGGRGRGR APERVGGRGR GRGTAAPRAA

121 PAARGSRPGP AGTMAAGSIT TLPALPEDGG SGAFPPGHFK DPKRLYCKNG GFFLRIHPDG

181 RVDGVREKSD PHIKLQLQAE ERGVVSIKGV CANRYLAMKE DGRLLASKCV TDECFFFERL

241 ESNNYNTYRS RKYTSWYVAL KRTGQYKLGS KTGPGQKAIL FLPMSAKS
```

Purified IGF or FGF2 or fragments thereof that stimulate or mobilize Ctsk-positive is administered directly into the synovial fluid or joint space.

Standard methods for delivery of peptides or cells are used. Such methods are well known to those of ordinary skill in the art, e.g., For intra-articular administration, peptides are delivered to the synovial cavity at a concentration in the range of 10-1000 ug/ml in a volume of approximately 0.1-2 ml per injection. For example, 1 ml of a peptide at a concentration of 250 ug/ml is injected into a joint using a fine (e.g., 14-22 gauge, preferably 18-22 gauge) needle. For administration of cells, $1\times10^4$-$1\times10^{10}$ cells are injected into a joint in approximately the same volume (1 ml). Volumes and concentrations of active compositions are adjusted depending on the size of the joint and joint space.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims. The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

The invention claimed is:

1. A method of repairing, restoring, or producing articular cartilage comprising introducing into an articulating joint an enriched population of cells comprising at least 60% cathepsin K positive cartilaginous stem cells, wherein said population comprises cells isolated from a perichondrial groove of Ranvier, wherein the population is harvested from groove of Ranvier cells from human cartilage and purified using a Cathepsin K-specific reagent.

2. The method of claim 1, wherein said population of cathepsin K positive cartilaginous stem cells comprises autologous, allogeneic or syngeneic cathepsin K positive cartilaginous stem cells.

3. The method of claim 1, further comprising administering to said articulating joint an agent, wherein said agent mobilizes and/or stimulates cathepsin K-expressed stem cells.

4. The method of claim 3, wherein said agent comprises insulin growth factor (IGF) or fibroblast growth factor 2 (FGF2).

5. The method of claim 1, wherein said articulating joint comprises a knee, hip, elbow, shoulder or vertebra.

6. The method of claim 1, wherein said population of stem cells comprises $1 \times 10^4$-$1 \times 10^{10}$ cells.

7. The method of claim 1, wherein said introducing comprises an intra-articular administration.

8. The method of claim 1, wherein said enriched population of cells comprises at least 70% cathepsin K positive cartilaginous stem cells.

9. The method of claim 1, wherein said enriched population of cells comprises at least 75% cathepsin K positive cartilaginous stem cells.

10. The method of claim 1, wherein said enriched population of cells comprises at least 80% cathepsin K positive cartilaginous stem cells.

11. The method of claim 1, wherein said enriched population of cells comprises at least 85% cathepsin K positive cartilaginous stem cells.

12. The method of claim 1, wherein said enriched population of cells comprises at least 90% cathepsin K positive cartilaginous stem cells.

13. The method of claim 1, wherein said enriched population of cells comprises at least 95% cathepsin K positive cartilaginous stem cells.

14. The method of claim 1, wherein said enriched population of cells comprises at least 98% cathepsin K positive cartilaginous stem cells.

15. The method of claim 1, wherein said enriched population of cells comprises at least 99% cathepsin K positive cartilaginous stem cells.

16. The method of claim 1, wherein said Cathepsin K-specific reagent comprises an anti-Cathepsin K antibody.

\* \* \* \* \*

SEQUENCE LISTING

<160> NUMBER OF SEQ ID NOS: 3

<210> SEQ ID NO 1
<211> LENGTH: 329
<212> TYPE: PRT
<213> ORGANISM: Homo sapiens

<400> SEQUENCE: 1

Met Trp Gly Leu Lys Val Leu Leu Pro Val Val Ser Phe Ala Leu
1               5                   10                  15

Tyr Pro Glu Glu Ile Leu Asp Thr His Trp Glu Leu Trp Lys Lys Thr
            20                  25                  30

His Arg Lys Gln Tyr Asn Asn Lys Val Asp Glu Ile Ser Arg Arg Leu
            35                  40                  45

Ile Trp Glu Lys Asn Leu Lys Tyr Ile Ser Ile His Asn Leu Glu Ala
        50                  55                  60

Ser Leu Gly Val His Thr Tyr Glu Leu Ala Met Asn His Leu Gly Asp
65                  70                  75                  80

Met Thr Ser Glu Glu Val Val Gln Lys Met Thr Gly Leu Lys Val Pro
                85                  90                  95

Leu Ser His Ser Arg Ser Asn Asp Thr Leu Tyr Ile Pro Glu Trp Glu
                100                 105                 110

Gly Arg Ala Pro Asp Ser Val Asp Tyr Arg Lys Lys Gly Tyr Val Thr
                115                 120                 125

Pro Val Lys Asn Gln Gly Gln Cys Gly Ser Cys Trp Ala Phe Ser Ser
            130                 135                 140

Val Gly Ala Leu Glu Gly Gln Leu Lys Lys Lys Thr Gly Lys Leu Leu
145                 150                 155                 160

Asn Leu Ser Pro Gln Asn Leu Val Asp Cys Val Ser Glu Asn Asp Gly
                165                 170                 175

Cys Gly Gly Gly Tyr Met Thr Asn Ala Phe Gln Tyr Val Gln Lys Asn
                180                 185                 190

Arg Gly Ile Asp Ser Glu Asp Ala Tyr Pro Tyr Val Gly Gln Glu Glu
            195                 200                 205

Ser Cys Met Tyr Asn Pro Thr Gly Lys Ala Ala Lys Cys Arg Gly Tyr
        210                 215                 220

Arg Glu Ile Pro Glu Gly Asn Glu Lys Ala Leu Lys Arg Ala Val Ala
225                 230                 235                 240

Arg Val Gly Pro Val Ser Val Ala Ile Asp Ala Ser Leu Thr Ser Phe
                245                 250                 255

Gln Phe Tyr Ser Lys Gly Val Tyr Tyr Asp Glu Ser Cys Asn Ser Asp
                260                 265                 270

Asn Leu Asn His Ala Val Leu Ala Val Gly Tyr Gly Ile Gln Lys Gly
            275                 280                 285

Asn Lys His Trp Ile Ile Lys Asn Ser Trp Gly Glu Asn Trp Gly Asn
        290                 295                 300

Lys Gly Tyr Ile Leu Met Ala Arg Asn Lys Asn Asn Ala Cys Gly Ile
305                 310                 315                 320

Ala Asn Leu Ala Ser Phe Pro Lys Met
                325

<210> SEQ ID NO 2
<211> LENGTH: 195
<212> TYPE: PRT
<213> ORGANISM: Homo sapiens

<400> SEQUENCE: 2

```
Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
            20                  25                  30

Phe Tyr Leu Ala Leu Cys Leu Leu Thr Phe Thr Ser Ser Ala Thr Ala
        35                  40                  45

Gly Pro Glu Thr Leu Cys Gly Ala Glu Leu Val Asp Ala Leu Gln Phe
    50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
        115                 120                 125

Met Pro Lys Thr Gln Lys Tyr Gln Pro Pro Ser Thr Asn Lys Asn Thr
    130                 135                 140

Lys Ser Gln Arg Arg Lys Gly Trp Pro Lys Thr His Pro Gly Gly Glu
145                 150                 155                 160

Gln Lys Glu Gly Thr Glu Ala Ser Leu Gln Ile Arg Gly Lys Lys Lys
                165                 170                 175

Glu Gln Arg Arg Glu Ile Gly Ser Arg Asn Ala Glu Cys Arg Gly Lys
            180                 185                 190

Lys Gly Lys
        195

<210> SEQ ID NO 3
<211> LENGTH: 288
<212> TYPE: PRT
<213> ORGANISM: Homo sapiens

<400> SEQUENCE: 3

Met Val Gly Val Gly Gly Gly Asp Val Glu Asp Val Thr Pro Arg Pro
1               5                   10                  15

Gly Gly Cys Gln Ile Ser Gly Arg Gly Ala Arg Gly Cys Asn Gly Ile
            20                  25                  30

Pro Gly Ala Ala Ala Trp Glu Ala Ala Leu Pro Arg Arg Arg Pro Arg
        35                  40                  45

Arg His Pro Ser Val Asn Pro Arg Ser Arg Ala Ala Gly Ser Pro Arg
    50                  55                  60

Thr Arg Gly Arg Arg Thr Glu Glu Arg Pro Ser Gly Ser Arg Leu Gly
65                  70                  75                  80

Asp Arg Gly Arg Gly Arg Ala Leu Pro Gly Gly Arg Leu Gly Gly Arg
                85                  90                  95

Gly Arg Gly Arg Ala Pro Glu Arg Val Gly Gly Arg Gly Arg Gly Arg
            100                 105                 110

Gly Thr Ala Ala Pro Arg Ala Ala Pro Ala Ala Arg Gly Ser Arg Pro
        115                 120                 125

Gly Pro Ala Gly Thr Met Ala Ala Gly Ser Ile Thr Thr Leu Pro Ala
    130                 135                 140

Leu Pro Glu Asp Gly Gly Ser Gly Ala Phe Pro Pro Gly His Phe Lys
145                 150                 155                 160
```

```
Asp Pro Lys Arg Leu Tyr Cys Lys Asn Gly Phe Phe Leu Arg Ile
            165                 170                 175

His Pro Asp Gly Arg Val Asp Gly Val Arg Glu Lys Ser Asp Pro His
            180                 185                 190

Ile Lys Leu Gln Leu Gln Ala Glu Glu Arg Gly Val Val Ser Ile Lys
            195                 200                 205

Gly Val Cys Ala Asn Arg Tyr Leu Ala Met Lys Glu Asp Gly Arg Leu
        210                 215                 220

Leu Ala Ser Lys Cys Val Thr Asp Glu Cys Phe Phe Phe Glu Arg Leu
225                 230                 235                 240

Glu Ser Asn Asn Tyr Asn Thr Tyr Arg Ser Arg Lys Tyr Thr Ser Trp
                245                 250                 255

Tyr Val Ala Leu Lys Arg Thr Gly Gln Tyr Lys Leu Gly Ser Lys Thr
            260                 265                 270

Gly Pro Gly Gln Lys Ala Ile Leu Phe Leu Pro Met Ser Ala Lys Ser
        275                 280                 285
```